US009827319B2

(12) United States Patent
Russell et al.

(10) Patent No.: US 9,827,319 B2
(45) Date of Patent: Nov. 28, 2017

(54) COMBINED THERAPY AND PROPHYLAXIS FOR GENITAL TRACT INFECTIONS

(71) Applicant: The Research Foundation for The State University of New York, Amherst, NY (US)

(72) Inventors: Michael W. Russell, East Amherst, NY (US); Yingru Liu, Snyder, NY (US); Nejat K. Egilmez, East Amherst, NY (US)

(73) Assignee: The Research Foundation for The State University of New York, Buffalo, NY (US)

( * ) Notice: Subject to any disclaimer, the term of this patent is extended or adjusted under 35 U.S.C. 154(b) by 0 days.

(21) Appl. No.: 14/404,197

(22) PCT Filed: May 29, 2013

(86) PCT No.: PCT/US2013/043068
§ 371 (c)(1),
(2) Date: Nov. 26, 2014

(87) PCT Pub. No.: WO2013/181224
PCT Pub. Date: Dec. 5, 2013

(65) Prior Publication Data
US 2015/0139941 A1 May 21, 2015

Related U.S. Application Data

(60) Provisional application No. 61/652,630, filed on May 29, 2012.

(51) Int. Cl.
*A61K 47/34* (2017.01)
*A61K 9/00* (2006.01)
*A61K 45/06* (2006.01)
*A61K 38/20* (2006.01)
*A61K 31/00* (2006.01)
*A61K 9/16* (2006.01)
*A61K 9/51* (2006.01)

(52) U.S. Cl.
CPC ............ *A61K 47/34* (2013.01); *A61K 9/0034* (2013.01); *A61K 9/1647* (2013.01); *A61K 9/5153* (2013.01); *A61K 31/00* (2013.01); *A61K 38/208* (2013.01); *A61K 45/06* (2013.01)

(58) Field of Classification Search
None
See application file for complete search history.

(56) References Cited

U.S. PATENT DOCUMENTS

| 6,509,313 | B1 * | 1/2003 | Smith ................ A61K 38/2013 424/184.1 |
|---|---|---|---|
| 2003/0212028 | A1 | 11/2003 | Raz et al. |
| 2007/0066545 | A1 | 3/2007 | El-Refaey |
| 2009/0022755 | A1 | 1/2009 | Barth et al. |
| 2009/0304722 | A1 | 12/2009 | Theisen et al. |

OTHER PUBLICATIONS

Mahapatro et al (Journal of Nanobiotechnology; 2011: 9:55).*
Lu et al (Molecular Medicine 6(7): 604-612, 2000).*
Perry et al (J Immunol 1997; 158:3344-3352.*
Wang, C., et al., Interleukin (IL)-2 and IL-12 responses to Chlamydia trachomatis infection in adolescents, Clinical and Experimental Immunology, Aug. 24, 2005, vol. 142, pp. 548-554.
Egilmez, N., et al., Tumor Vaccination with Cytokin-Encapsulated Microspheres, Methods in Molecular Medicine, Lung Cancer vol. II Diagnostic and Therapeutic Methods and Reviews, 2003, vol. 75, pp. 687-696.

* cited by examiner

*Primary Examiner* — Brian Gangle
*Assistant Examiner* — Andrea K McCollum
(74) *Attorney, Agent, or Firm* — Hodgson Russ LLP (57) ABSTRACT

Provided is a method for treating and reducing the recurrence of genital tract infections such as gonococcal infections. The method comprises local application of IL-12 incorporated in polymeric microspheres. The invention relates to compositions comprising IL-12 and methods for using such compositions for treatment of genital tract infections. Infections that can be treated by the present method include those that are caused by *N. gonorrhoeae, C. trachomatis* or both.

22 Claims, 10 Drawing Sheets

COMBINED THERAPY AND PROPHYLAXIS FOR GENITAL TRACT INFECTIONS

CROSS-REFERENCE TO RELATED APPLICATIONS

This application claims priority to U.S. Provisional Application No. 61/652,630, filed on May 29, 2012, the disclosure of which is incorporated herein by reference.

STATEMENT REGARDING FEDERALLY SPONSORED RESEARCH

This invention was made with government support under grant AI074791 awarded by the National Institutes of Health. The government has certain rights in the invention.

FIELD OF THE INVENTION

The invention relates to compositions comprising IL-12 and methods for using such compositions for treatment of genital tract infections.

BACKGROUND OF THE INVENTION

Genital tract infection by *Neisseria gonorrhoeae* gives rise to gonorrhea, which is the second most frequent reportable infectious disease in the US affecting >300,000 individuals per annum, although the real incidence is believed to be at least double that number. The worldwide incidence of gonorrhea is estimated to be >100 million cases per year. Women bear the brunt of the infection, because untreated gonorrhea can ascend into the upper reproductive tract and give rise to pelvic inflammatory disease and tubal scarring, leading to infertility and risk for ectopic pregnancy which can be life-threatening. Yet a large proportion of infected women, variously given as up to 50% or even more, can be asymptomatically infected, thereby increasing the risk of spreading the infection among their sexual contacts. Men by contrast usually become aware of their infection within a few days and are therefore impelled to seek treatment. New-born infants can become infected in the eyes as a result of delivery through an infected birth canal, and this can lead to blindness if left untreated. Untreated gonorrhea is also known to increase the risk for acquiring and transmitting HIV up to 5-fold. Treatment depends upon antibiotics, but *N. gonorrhoeae* has quickly become resistant to each class of antibiotics used against it, including most recently the fluorquinolones (ciprofloxacin), and the currently recommended antibiotics are cephalosporins. However, resistance to these has begun to emerge, making *N. gonorrhoeae* multiple-drug-resistant. Despite various efforts, no vaccine against *N. gonorrhoeae* is currently available. Thus options for treatment and control of the disease are becoming limited. A puzzling but well-known feature of gonorrhea is that recovery from infection does not lead to protective immunity against re-infection, and repeated infections are common.

SUMMARY OF THE INVENTION

The present invention provides a method for treatment of cervico-vaginal infections by local application of IL-12 incorporated in polymeric microspheres. While not intending to be bound by any particular theory, it is considered that application of IL-12 incorporated in polymeric microspheres locally to mucosal surfaces enhances the body's own immune response against an existing infection resulting in reduction or elimination of that infection and/or generation of immunity against repeat infection. In one embodiment, the amount is sufficient to promote Th1-driven response against the microorganisms causing the infection. The amount of IL-12 may be sufficient to provide a therapeutic effect, a prophylactic effect, or both against the causative microorganisms. Infections that can be treated by the present method include, but are not limited to, those that are caused by *N. gonorrhoeae, C. trachomatis* or both. An example of a polymer that can be used for microencapsulation of IL-12 is polylactic acid.

BRIEF DESCRIPTION OF THE DRAWINGS

For a fuller understanding of the nature and objects of the invention, reference should be made to the following detailed description taken in conjunction with the accompanying drawings, in which:

FIG. 4 is a graph showing the effect of intravaginal IL-12 microsphere (ms) treatment on primary gonococcal infection in BALB/c mice. (A) IL-12 ms dose optimization experiment. Microspheres containing the stated doses of IL-12 were given on days 0, 2, 4, 6, 8; n=8 mice per group. *N. gonorrhoeae* (Ngo) burden was monitored daily by vaginal swab culture. Significant differences in infection burdens were found between mice treated with 2.0 μg ($p<0.01$), 1.0 μg ($p<0.01$), or 0.5 μg ($p<0.05$) of microencapsulated IL-12 and controls (ANOVA). (B) Time course of infection in mice treated with IL-12 ms, soluble IL-12, IL-17 ms, or control ms, or in untreated mice; cytokine dose=1.0 μg given on days −1, 1, 3, 5, 7; n=8 mice per group. Significant differences in infection burdens were found between mice treated with IL-12 ms ($p<0.01$) or IL-17 ms ($p\sim 0.01$) and controls (ANOVA). (C) Data from the experiment shown in B plotted as percentage of mice remaining infected under the indicated cytokine treatments. Infection was cleared significantly faster in mice treated with IL-12 ms ($p<0.0001$) or IL-17 ms ($p<0.001$) than in controls (Kaplan-Meier). (D) Cytokine expression in isolated ILN cells from sham-infected or infected mice with IL-12 ms, IL-17 ms, or control ms treatment; n=7 mice per group. Expression of IFN-γ, IL-4, and IL-17 in $CD4^+$ T cells isolated at day 5 after infection was analyzed by flow cytometry. (E) RT-PCR analysis of IFN-γ, IL-4, and IL-17 mRNA levels in vaginal tissue harvested at day 3 from sham-infected or infected mice with IL-12 ms, IL-17 ms, or control ms treatment; n=7 mice per group. Cytokine gene expression levels detected by RT-PCR were normalized relative to expression of β-actin and set at 1.0 for sham-infected group. (F) Phenotypic profile of vaginal cells isolated on day 5 from sham-infected or infected mice treated with IL-17 ms or control ms; n=7 mice per group. (G) Vaginal and (H) serum anti-gonococcal IgA and IgG antibody responses in sham-infected or infected mice with IL-12 ms, IL-17 ms, or control ms treatment; n=7 mice per group.

Vaginal washes and sera were collected 15 days after inoculation, and gonococcus-specific and total IgA and IgG were measured by ELISA. Results from one representative out of three independent experiments are shown. In D-H, #p<0.05; * p<0.01 (unpaired t test);

FIG. 5 is a graph showing the effect of intravaginal IL-12 microsphere (ms) treatment during primary infection on secondary gonococcal infection. (A) Time course of secondary infection in mice treated with IL-12 ms, soluble IL-12, IL-17 ms, or control ms during primary infection, or in previously sham-infected mice with or without IL-12 ms treatment; n=8 mice per group. Significant differences in infection burdens were found between mice previously treated with IL-12 ms (p ~0.01) and controls (ANOVA). (B) Data from the experiment shown in A plotted as percentage of mice remaining infected after reinfection under the indicated treatments during primary infection. Infection was cleared significantly faster in mice previously treated with IL-12 ms (p<0.0001) than in controls (Kaplan-Meier). (C) Flow cytometric analysis of cytokine expression in ILN $CD4^+$ T cells isolated at day 5 from reinfected mice treated with IL-12 ms, IL-17 ms, or control ms during primary infection, or from mice that were sham-infected in both primary and secondary phases ("sham-reinfected"); n=7 mice per group. (D) RT-PCR analysis of IFN-γ, IL-4, and IL-17 mRNA levels in vaginas harvested at day 3 from sham-reinfected or reinfected mice treated with IL-12 ms, IL-17 ms, or blank ms during primary infection; n=7 mice per group. Cytokine gene expression levels detected by RT-PCR were normalized relative to expression of β-actin and set at 1.0 for sham-reinfected group. (E) Vaginal and (F) serum anti-gonococcal IgA and IgG antibody responses to secondary infection in sham-reinfected or reinfected mice treated with IL-12 ms, IL-17 ms, or blank ms during primary infection; n=7 mice per group. Vaginal washes and sera were collected 15 days after inoculation, and gonococcus-specific and total IgA and IgG were measured by ELISA. Results from one representative out of three independent experiments are shown. In C-F, #p<0.05; * p<0.01 (unpaired t test).

DESCRIPTION OF THE INVENTION

The present invention is based on our studies which have helped to unfold the ways in which *N. gonorrhoeae* prevents the immune system from mounting effective immune responses against it. We provide here a novel approach to overcome the ability of *N. gonorrhoeae* to suppress immune response against it.

In one embodiment, the present invention provides a method of treating genital tract infections in a female subject by intravaginal application of IL-12 incorporated in polymeric microspheres. The infections that can be treated by this method include bacterial, fungal, parasitic, viral and the like. In one embodiment, the amount is sufficient to promote Th1-driven response against the microorganisms causing the infection. In one embodiment, the amount is sufficient to provide a therapeutic effect, a prophylactic effect, or both against the causative microorganisms. The term "treated" or "treatment" as used herein means to reduce or eliminate an infection. An infection is considered to be reduced when the underlying cause of the infection is reduced.

In one embodiment, the method of the present invention is useful for treating genital tract infections, such as cervico-vaginal infections, caused by bacteria, such as *N. gonorrhoeae*. The method comprises the steps of providing local (intravaginal) application of the cytokine interleukin-12 (IL-12) incorporated in biodegradable, biocompatible microspheres. In one embodiment, the dose is sufficient to promote Th1-driven immune responses against infection with *N. gonorrhoeae*. In one embodiment, the invention provides a method for therapy or prophylaxis or both for cervico-vaginal gonococcal infection (i.e., gonorrhea) by means of local administration of IL-12 microspheres. While not intending to be bound by any particular theory, it is considered that this method works, at least in part, by reversing the ability of *N. gonorrhoeae* to interfere with the host's immune responses.

In one embodiment, the IL-12 formulation is delivered locally to the mucosal surface of the genital tract of an individual. In one embodiment, the individual is not already receiving IL-12, or has not been administered IL-12 prior to the initiation of the present method. In one embodiment, the individual is not receiving IL-12 via any other administration mode. In one embodiment, the formulation contains no other therapeutic agent, no other prophylactic agent, or no other agent that is both therapeutic and prophylactic. In one embodiment, the formulation does not contain the infection causing microorganism (such as in an inactivated form) or an antigen therefrom, and the individual has not been and/or is not being administered the inactivated microorganism or an antigen therefrom. In another embodiment, the formulation may be delivered to an individual who is already receiving treatment (other than IL-12) for genital tract infection (such as gonococcal infection).

In one embodiment, the invention further comprises the step of administering an antimicrobial agent to the individual. For example, in one embodiment, the method of this invention comprises the steps of identifying an individual who is suffering from or has been diagnosed with an infection of the genital tract, delivering to the genital tract locally (such as intravaginally) a composition comprising a therapeutically effective, a prophylactically effective, or both therapeutically and prophylactically effective amount of a composition comprising IL-12 in biodegradable polymeric microspheres, and optionally administering to the individual one or more antimicrobial agents (such as antibiotics, antifungal or antiviral agents). The antimicrobial agents may be administered prior to, during or after the administration of the IL-12 formulation. An example of such a treatment is the administration of antibacterial agents, such as antibiotics. Examples of suitable antibiotics used for genital tract infections include fluorquinolones, cephalosporins, azithromycin, Ceftriaxone, doxycycline, and Cefixime.

In one embodiment, the IL-12 formulations of the present invention are sustained release formulations. In one embodiment, IL-12 is delivered as incorporated (also referred to herein as encapsulated or microencapsulated) in polymeric microparticles (also referred to herein as microspheres). In one embodiment, the microparticles are biodegradable and biocompatible. Preparation techniques for such microspheres are known in the art. See for example, U.S. Pat. Nos. 6,143,211; 6,235,244; 6,616,869; and 7,029,700, the disclosures of which pertaining to methods and compositions for preparation of microspheres are incorporated herein by reference. In one embodiment, a phase inversion technique is used to prepare microencapsulated IL-12. In general, a biodegradable polymer is dissolved in a solvent (such as dichloromethane or other organic solvent) and then a mixture is formed by adding micronized IL-12 (i.e. lyophilized mixtures of IL-12 and excipient such as polyvinyl pyrrolidone) to the polymer dissolved in the solvent. A non-solvent (such as alcohol or hexane) is then introduced causing spontaneous formation of microencapsulated IL-12. Examples of biodegradable polymers include polymers of lactic acid and glycolic acid, polyanhydrides, poly(ortho) esters, polyurethanes, poly(butyric acid), poly(valeric acid), poly(caprolactone), poly(hydroxybutyrate), poly(lactide-co-glycolide) and poly(lactide-co-caprolactone), and natural polymers. In one embodiment, the microspheres are composed of a polymer of lactic acid (polylactic acid (PLA)).

In one embodiment, the IL-12 containing microspheres degrade by hydrolysis slowly over time, releasing the encapsulated IL-12. The microspheres are suspended before use and can also be delivered in an acceptable buffered physiological saline solution. In one embodiment, slow release of IL-12 over a period of time such as approximately 4 days allows for continuous stimulation of locally present immune cells without elevating the concentration of IL-12 in the local tissues or the circulation to potentially harmful levels. The microspheres are made of biodegradable materials. In one embodiment, the hydrolytic product of the microspheres is lactic acid, a harmless product of normal metabolism. PLA is a component of absorbable sutures and has been in use for that purpose for many decades, and is therefore considered safe. Microencapsulated IL-12 has been shown to be stable in storage at ambient temperatures and to have a long shelf-life.

The microspheres are in the range of 10 nm to 10 microns. The microspheres may be suspended in pharmaceutically acceptable medium such as a physiological buffer. In one embodiment, the loading of IL-12 is from 0.1 to 10 µg per mg of the particles. In one embodiment, the loading is from 1 to 5 µg IL-12 per mg of the particles. In one embodiment, the loading is from about 2.5 µg IL-12 per mg of the particles.

The IL-12 formulations can be used in amounts that will result in therapeutic and/or prophylactic effects. An effective dose in mice was observed to be 1 µg of IL-12. Determining the effective dosage for humans is within the purview of clinicians and other individuals involved in the treatment of such infections. Generally, the amount administered depends upon various factors including the severity of the infection, the weight, health and age of the individual. Such factors can be readily determined by a clinician. In one embodiment, the dose may be from 1 µg to 200 µg of IL-12 per day. In some embodiments, the dose is 1, 5, 10, 15, 20, 50, 75, 100, 125, 150, 175 and 200 µg of IL-12 per dose and all integers between 1 and 200 µg and all ranges therebetween. The dosage required may be less if used in conjunction with an antimicrobial agent.

The dosage may be repeated as necessary. For example, the administration may be repeated daily, multiple times in a day, or at longer intervals, such as at intervals of 2-4 days, weekly or monthly. In one embodiment, the administration is repeated at intervals from 1 day to 1 month (28, 29, 30 or 31 days) or beyond that and all intervals therebetween. The treatment regimen may be repeated as necessary. In some embodiments, the dosage is administered every 2, 3, 4, 5, 6, 7, 10, or 14 days, or longer.

In one embodiment, the administration of the microencapsulated IL-12 as described here reduces the *N. gonorrhoeae* infection. In one embodiment, the infection is eliminated. The presence or absence of infection or the level of infection may be tested by routine microbiological methods (such as culture and testing). In one embodiment, the infection may be tested by obtaining vaginal swab and testing for the presence of bacteria (such as by the ability to form colonies), or by nucleic acid amplification methods.

In another embodiment, the administration of the microencapsulated IL-12 as described here reduces the *N. gonorrhoeae* infection and reduces the risk of repeat infection of *N. gonorrhoeae* after the treatment with microencapsulated IL-12 has been stopped. While not intending to be bound by any particular theory, it is considered that the prophylactic effect of IL-12 is achieved by stimulation of the immune system. In one embodiment, the administration of IL-12 does not significantly increase the level of IL-12 in the systemic circulation. In one embodiment, the serum level of IL-12 does not increase to greater than 50 picograms/ml.

For intravaginal applications, the formulations of the present invention can be delivered as applied to an article of manufacture acting as a carrier. For example, the formulations may be incorporated into or onto and then delivered via an insert, an applicator, tablet, suppository, vaginal ring, vaginal sponge, tampon and the like. The formulation may also be delivered in the form of a liquid, cream, gel, lotion, ointment, paste, spray and the like.

The pharmaceutical formulations may optionally include pharmaceutically acceptable carriers, buffers, diluents, solubilizing or emulsifying agents, and various salts. Such additives are well known in the art. See, e.g., Remington's Pharmaceutical Sciences, 18th Ed. (1990, Mack Publishing Co., Easton, Pa. 18042).

An advantage of local application of microencapsulated IL-12 as described herein is that it can provide a sustained effect while avoiding problems of potential systemic toxicity.

In one embodiment, the present invention is used for treating genital *Chlamydia trachomatis* infection (*chlamydia*). *Chlamydia* is another sexually transmitted disease (STD) of even more frequent occurrence than gonorrhea, and is the most frequently reported infectious disease in the US, thought to affect up to 3 million individuals per annum (>92 million worldwide). It is also a major cause of pelvic inflammatory disease in women and its sequelae (infertility and risk for ectopic pregnancy). Therefore in one embodiment, local (intravaginal) application of IL-12 incorporated in polymeric microspheres is used to promote local Th1-immune responses for therapy and prophylaxis against *C. trachomatis*. In one embodiment, the method of the present invention is used to treat urinogenital infections due to *N. gonorrhoeae* and *C. trachomatis*. This may be advantageous in the STD clinic setting because gonorrhea and *chlamydia* present with similar signs and symptoms, and the differential diagnosis may depend on identifying the causative organism. Furthermore, mixed infections with both are common. In other embodiments, other genital tract infections could also be treated with (intravaginal) application of microencapsulated IL-12 to enhance local immunity against them.

In other embodiments, local application of microencapsulated IL-12 is used in the treatment of other local mucosal infections where the normal immune response is insufficient to eliminate them. Examples include: bronchitis and chronic obstructive pulmonary disease (respiratory tract), otitis media (middle ear infection, which is the most frequent reason for pediatric office visits in the US), *Helicobacter pylori* infection (which causes gastric ulcer and can lead to gastric cancer), and possibly periodontal disease (which afflicts most adults from age 35 onwards and is the main cause of tooth loss in adults).

EXAMPLE 1

The invention has been demonstrated in the mouse model of vaginal gonococcal infection. Details of the mouse model can be found in Jerse, *Infect. Immun.* 67: 5699-5708; 1999.

Figure 1:
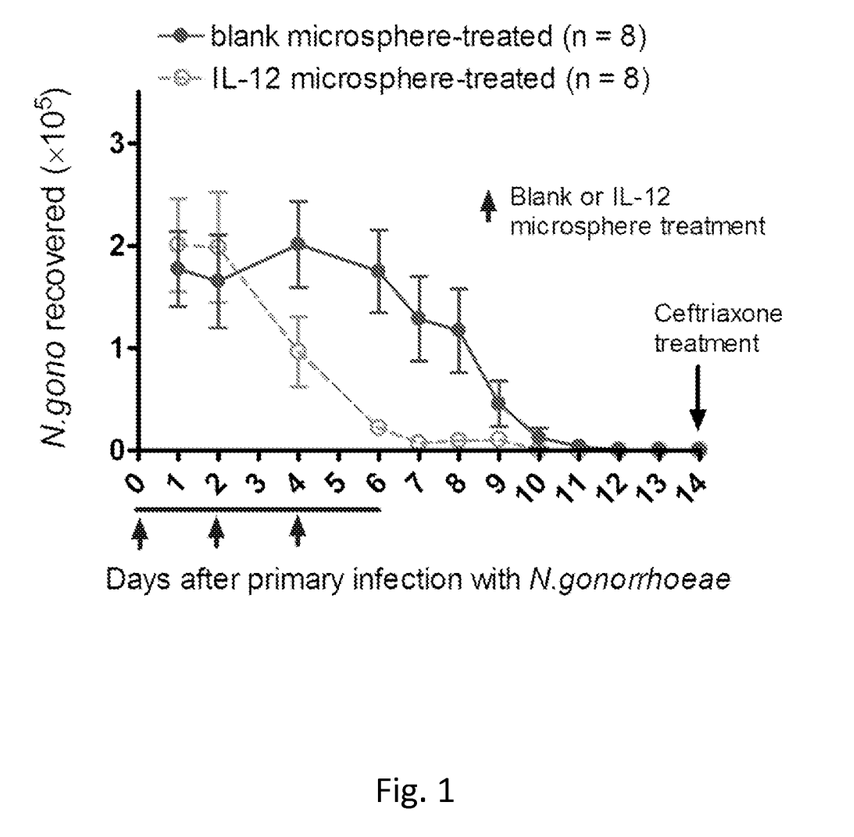
FIG. 1 is a graph showing the effects of intravaginal treatment with 1 μg of IL-12 encapsulated in polylactic acid (PLA) microspheres on the course of vaginal infection with *N. gonorrhoeae* in mice.

Intravaginal treatment of mice with IL-12 microspheres (1 µg) on days 0, 2, and 4 of primary vaginal infection (on day 0) with N. gonorrhoeae resulted in accelerated clearance of the infection, compared to control mice given blank microspheres (See FIG. 1).

FIG. 1 illustrates the effect of intravaginal treatment with 1 µg of IL-12 encapsulated in PLA microspheres (on days 0, 2, and 4) on the course of vaginal infection with N. gonorrhoeae in mice. Data shown as mean±SEM cfu of N. gonorrhoeae recovered from vaginal swabs taken daily; N=8 mice per group. Control mice were given blank microspheres. Mice were treated with antibiotic on day 14 and then rested for secondary infection (See FIG. 2).

When mice that were treated with IL-12 microspheres during primary vaginal gonococcal infection were allowed to recover, treated with antibiotic (ceftriaxone) on day 14, rested and then reinfected one month later with N. gonorrhoeae, the secondary infection was cleared faster than in control mice given blank microspheres during primary infection (See FIG. 2). Normally, secondary infection is considered to clear with the same kinetics as primary infection, and there is little or no antibody response developed.

Figure 2:
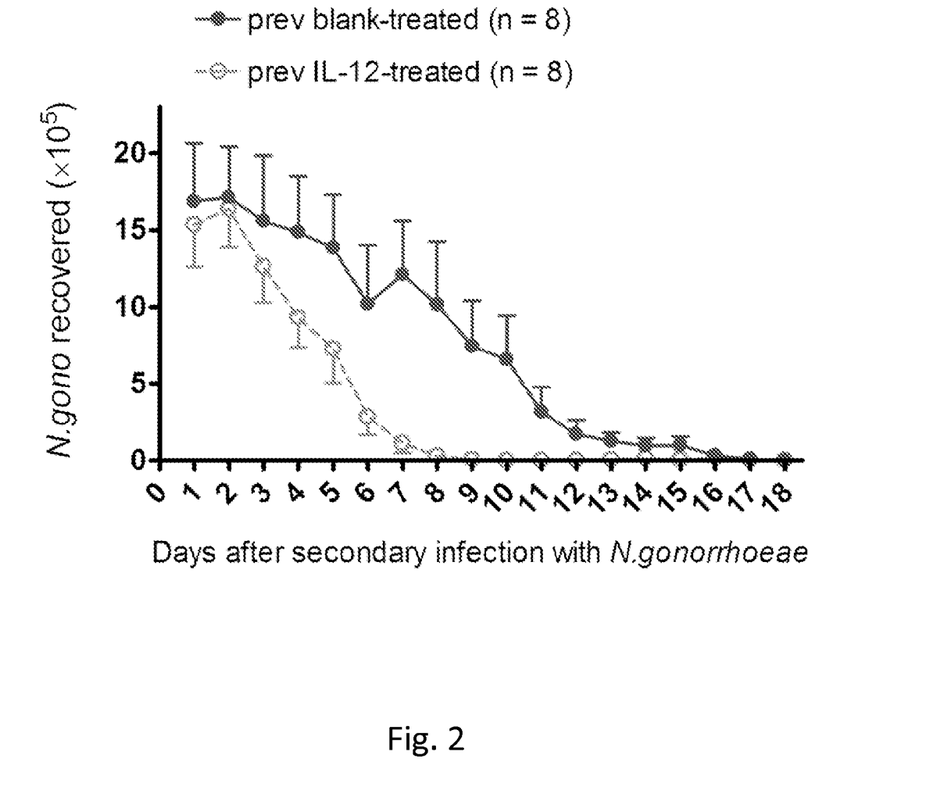
FIG. 2 is a graph showing the effects of intravaginal treatment with IL-12 microspheres during primary infection with *N. gonorrhoeae* (FIG. 1) on the course of secondary vaginal infection with *N. gonorrhoeae* in mice.

FIG. 2 illustrates the effect of intravaginal treatment with IL-12 microspheres during primary infection with N. gonorrhoeae (See FIG. 1) on the course of secondary vaginal infection with N. gonorrhoeae in mice. Control mice were given blank microspheres. Data shown as mean±SEM cfu of N. gonorrhoeae recovered from vaginal swabs taken daily; N=8 mice per group.

Figure 3:
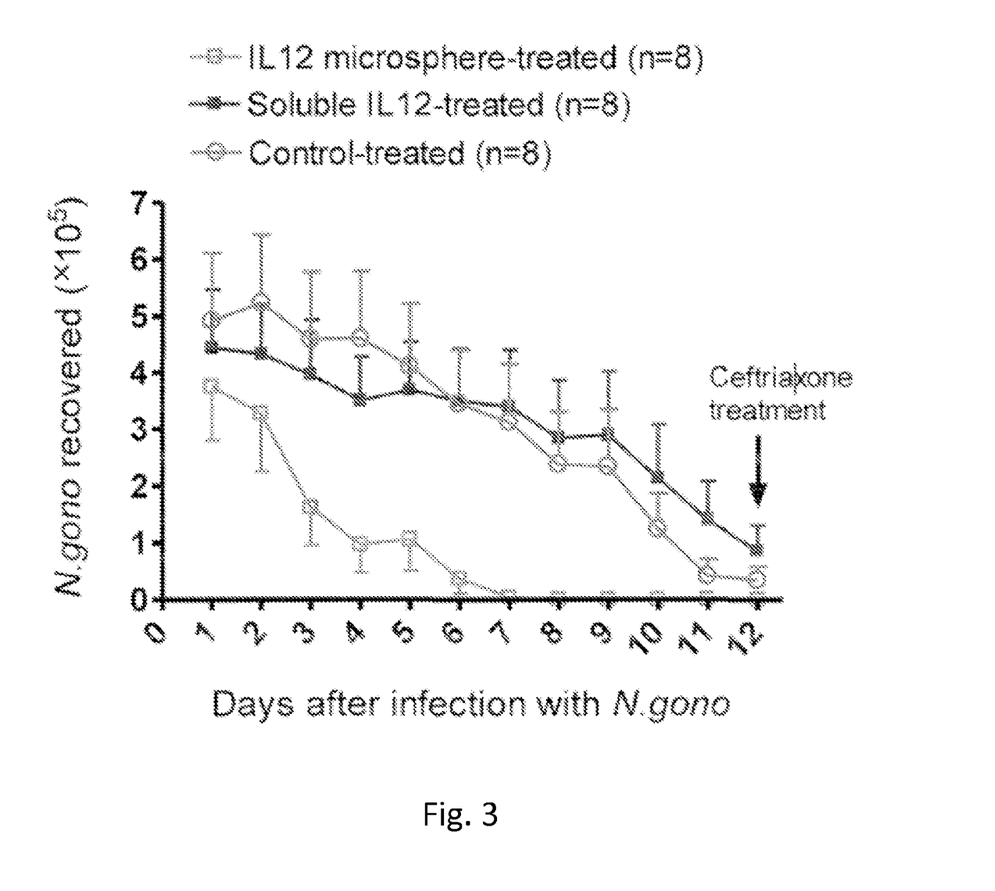
FIG. 3 is a graph showing the effects of intravaginal treatment with 1 μg of soluble vs. microencapsulated IL-12 on the course of vaginal infection with *N. gonorrhoeae* in mice.

Further, the effect of intravaginal treatment with microencapsulated IL-12 (IL-12 microspheres) was compared with soluble IL-12 on the course of mouse genital tract infection with *Neisseria gonorrhoeae*. For this purpose, 1 µg of IL-12 was instilled intravaginally in a group of 8 mice in free soluble form (dissolved in sterile phosphate-buffered physiological saline) on days 0, 2, 4, 6, 8, and 10 after infection with N. gonorrhoeae (i.e., every other day until the infection was cleared), in direct comparison with mice treated with IL-12 microspheres and a control group treated with vehicle only. Mice treated with IL-12 microspheres cleared the infection within 7 days, much faster than the control group, whereas mice treated with soluble IL-12 cleared the infection at the same rate as the control group (See FIG. 3). Data shown as mean±SEM cfu of N. gonorrhoeae recovered from vaginal swabs taken daily; N=8 mice per group.

The results show that local intravaginal treatment with soluble IL-12 had no effect on the course of infection, whereas IL-12 microspheres accelerated clearance, as described previously.

EXAMPLE 2

This example describes another set of experiments that illustrate the effectiveness of intravaginal application of IL-12 microspheres on N. gonorrhoeae vaginal infection.

Materials and Methods

Mice: BALB/c mice were purchased from Jackson Laboratories (Bar Harbor, Me.), and were maintained under standard conditions in the Laboratory Animal Facility at the University at Buffalo. All animal use protocols were approved by the Institutional Animal Care and Use Committee of the University at Buffalo.

Bacteria: N. gonorrhoeae FA1090 were cultured on GC agar supplemented with hemoglobin and ISOVITALEX, an enrichment medium (BD Diagnostic Systems, Franklin Lakes, NJ). Growth was checked for colony morphology consistent with Opa protein and pilus expression, and gonococci were harvested from plates and the cell density was determined. Opa expression as was: Opa A, B/D/G, E/K.

Microspheres: Cytokines were encapsulated into polylactic acid (PLA) microspheres using the Phase Inversion Nanoencapsulation (PIN) technology as follows. Briefly, recombinant IL-12 (mouse or human) is mixed with excipients including sucrose (0.1%, w/w) and polyvinylpyrrolidone in water and then is lyophilized. The lyophilized material is dissolved in tertyl butyl alcohol (TBA) and is mixed with polylactic acid (PLA) resomer dissolved in TBA (1 to 3 ratio, vol:vol for micronized IL-12 and PLA solution). This solution is then poured into 100× volume of heptane to induce formation of the particles. The particles are then filtered and lyophilized. Three formulations were produced: (a) control microspheres containing no cytokine or antibody; (b) murine IL-12 (0.25 µg/mg particles); and (c) murine IL-17 (0.25 µg/mg particles).

Mouse Vaginal Infection Model: Female mice between 7 and 9 weeks old were infected vaginally on day 0 with live N. gonorrhoeae FA1090 as previously described. Vaginal mucus was quantitatively cultured daily on GC agar supplemented with selective antibiotics to determine the bacterial colonization loads. The limit of detection was 100 CFU recovered per mouse. Intravaginal treatments with microsphere preparations were given every second day from day 0 to day 8, by instillation of 40 µl suspensions in PBS of microspheres containing IL-12 or IL-17, or control microspheres.

Cell Isolation and Flow Cytometry: Mice were sacrificed and the iliac lymph nodes (ILN) and genital tracts were excised aseptically. ILN were teased in Hanks' buffered salt solution to release cells. Vaginal single-cell suspensions were prepared by enzymatic digestion. Isolated cells were washed with staining buffer twice, then incubated with the indicated antibodies for 30 min on ice, washed twice, and analyzed on a FACSCalibur cytometer. For determination of intracellular cytokine expression, cells were restimulated with phorbol myristate acetate-ionomycin-GOLGISTOP, a protein transport inhibitor (eBioscience, San Diego, CA) for 5 h, and then fixed with CYTOFIX/CYTOPERM, a fixation/permeabilization solution (eBioscience). Antibodies to mouse CD4, CD8, CD19, CD11b, CD1 1c, NKG2D, Gr-1, IFN-γ, IL-4, and IL-17A conjugated with fluorescein isothiocyanate, phycoerythrin, or allophycocyanin were purchased from eBioscience.

Cytokine ELISA: IL-12p70, IFN-γ, IL-4, IL-5, and IL-17A levels in serum or vaginal wash samples were measured in triplicate using ELISA kits purchased from eBioscience.

Real-time RT-PCR: Total cellular RNA of whole vaginas harvested from the mice was isolated with RNEASY, RNA purification Mini Kits (Qiagen, Valencia, CA), and was transcribed to cDNA using the ISCRIPT cDNA synthesis kit (Bio-Rad, Hercules, CA). Real-time RT-PCR was performed on an ICYCLER IQ, real-time PCR detection system (Bio-Rad) using SYBRGREEN, a dye (Bio-Rad) for real-time monitoring of the PCR. Relative quantification of target genes was analyzed based on the threshold cycle (Ct) determined by Bio-Rad IQ5, an optical system software.

Assay of Serum and Mucosal Antibodies: Samples of saliva, vaginal wash, and serum were collected from individual mice on day 15 post-inoculation. Gonococcus-specific IgA, IgG, and IgM in saliva, sera, and vaginal washes and total IgA, IgG, and IgM concentrations in secretions were assayed by ELISA.

Statistical Analysis: Data are expressed as the means±standard errors of the means (SEM). Data on the effects of IL-12-, IL-17-, anti-TGF-β-, anti-IL-10-loaded versus blank microsphere treatments on vaginal *N. gonorrhoeae* infection were analyzed using repeated-measures analysis of variance (ANOVA) with Bonferroni corrected post-hoc testing of pair-wise comparisons. Kaplan-Meier analysis with log-rank testing was also used to compare infection clearance. Data from in vitro experiments were analyzed by unpaired two-tailed t tests to compare the mean values between two selected groups. P<0.05 was considered statistically significant.

Results

Intravaginal Administration of IL-12 Microspheres Protects Mice Against Genital Tract *N. gonorrhoeae* Infection. To examine the therapeutic effect of IL-12-loaded microspheres, groups of female BALB/c mice were infected with *N. gonorrhoeae* and the bacterial burden was monitored daily by vaginal swab culture. Preliminary dose-ranging experiments showed that intravaginal instillation of microspheres containing 1.0 µg of IL-12 every second day was sufficient to accelerate clearance of the infection relative to treatment with blank microspheres; no further enhancement of clearance was obtained with 2.0 µg of microencapsulated IL-12, and lower doses were progressively less effective (FIG. 4A).

Figure 4:
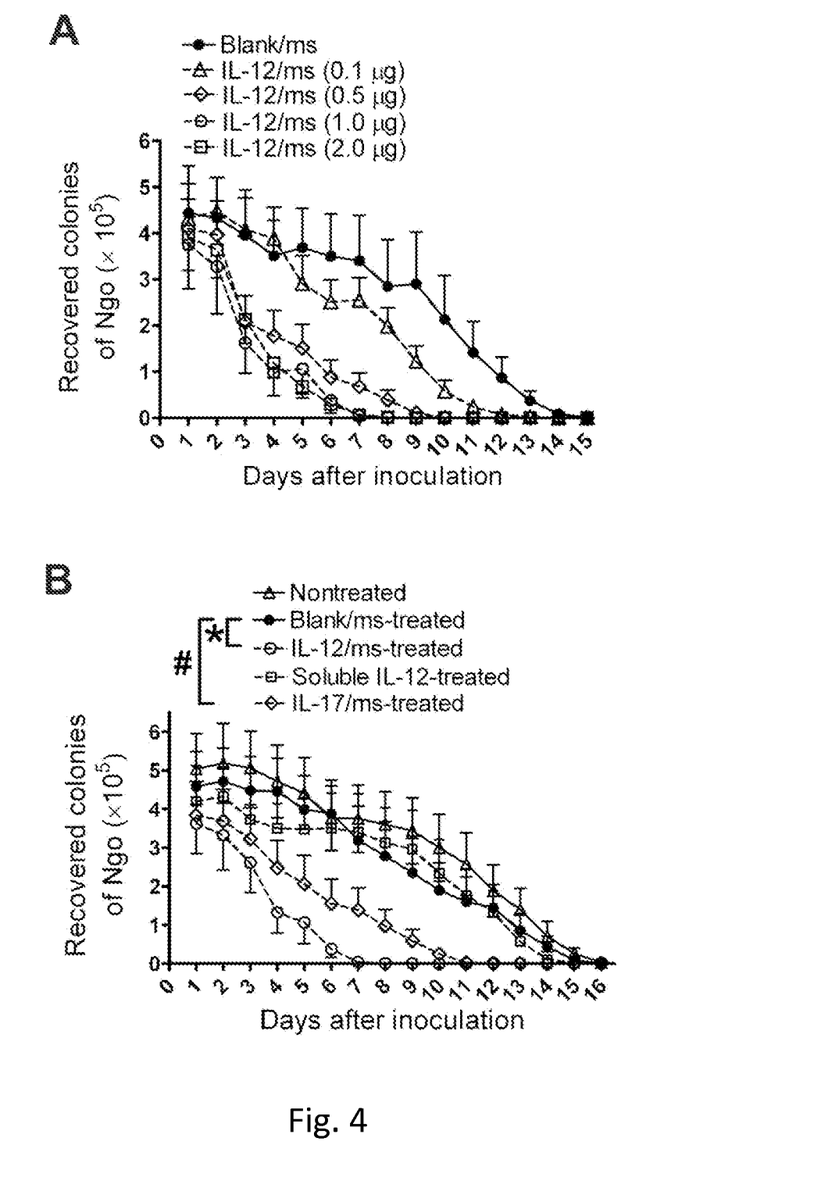

Untreated or blank microsphere-treated mice cleared the infection in ~15 days (FIG. 4B, C). Intravaginal instillation of microencapsulated IL-12 at the optimal 1.0 µg dose significantly reduced the recoverable *N. gonorrhoeae* load starting from day 4, and these mice cleared the infection by day 7, 8 days earlier than blank microsphere-treated or untreated mice (FIG. 4B, C). The infection did not relapse after treatment ceased on day 7. In contrast, intravaginal administration of free, soluble IL-12 was completely ineffective in enhancing clearance of *N. gonorrhoeae* (FIG. 4B, C).

Intravaginal administration of IL-17-loaded microspheres at the optimal dose (1.0 µg) also accelerated clearance of *N. gonorrhoeae* infection, but to a lesser extent than IL-12 microspheres given on the same schedule (FIG. 4B, C).

Treatment With IL-12 Microspheres Enhances Th1 and Antibody Responses to Vaginal Gonococcal Infection. To elucidate the mechanisms underlying the therapeutic effects of IL-12, we characterized the local immune responses to genital gonococcal infection in mice treated with IL-12-loaded or blank microspheres. Single-cell suspensions were prepared from ILN and vaginas of 7 mice per group at 3, 5, 7, and 14 days after inoculation with *N. gonorrhoeae* or vehicle only for evaluation by flow cytometry to detect intracellular IFN-γ, IL-4, and IL-17. Starting on day 3 after inoculation, IL-17$^+$/CD4$^+$ T cells were observed in the local draining ILN, with production peaking at day 5 and continuing for the duration of infection. At day 5, approximately 22% of CD4$^+$ T cells present in the ILN of control-treated infected mice were IL-17$^+$, whereas only ~3.5% were IFN-γ$^+$ and few IL-4$^+$/CD4$^+$ T cells were detected (FIG. 4D). IL-12 microsphere treatment markedly enhanced Th1 immune responses to *N. gonorrhoeae*, indicated by significantly increased numbers of IFN-γ$^+$/CD4$^+$ T cells (FIG. 4D). In contrast, IL-12 microspheres did not change Th2 or Th17 responses as the numbers of IL-4$^+$/CD4$^+$ and IL-17$^+$/CD4$^+$ T cells in ILN were similar between the treated groups (FIG. 4D). RT-PCR analyses showed that IFN-γ, but not IL-4 or IL-17 mRNA expression was elevated in the vaginas of infected mice following IL-12 microsphere treatment (FIG. 4E). Although IL-17 microspheres ameliorated gonococcal infection, this treatment was not associated with enhanced Th1 or Th2 responses (FIG. 4D, E), but there was increased influx of Gr-1$^+$ neutrophils into the genital tract (FIG. 4F).

We also measured by ELISA IL-12p70, IFN-γ, IL-4, and IL-17 concentrations in vaginal wash and serum collected 7 days after inoculation. IL-12 (176.5±48.6 pg/ml) was detected in vaginal wash from infected mice treated with IL-12 microspheres. Low levels of IL-12 (41.7±10.7 pg/ml) were found in the serum of these mice, suggesting that the effects of IL-12 microsphere treatment on gonococcal infection did not result primarily from the passage of the cytokine into the circulation. Consistent with the flow cytometric studies, IFN-γ was present in the vaginal wash (32.6±9.8 pg/ml) and serum (43.3±11.5 pg/ml) of infected mice treated with IL-12 microspheres, but IL-4 and IL-17 were not detected. None of these cytokines was detected in control-treated infected mice.

IL-12 can stimulate humoral immune responses in an IFN-γ-dependent manner or directly. We therefore determined whether IL-12 microsphere treatment during *N. gonorrhoeae* infection led to the production of anti-gonococcal antibodies in vaginal wash, saliva, and serum collected 15 days after inoculation. IgM antibodies were at low levels with little difference between experimental groups (data not shown). No salivary gonococcus-specific antibody was detected in any group of mice (data not shown). *N. gonorrhoeae* infection of control-treated mice did not significantly elevate gonococcus-specific IgA or IgG antibodies in either vaginal washes or sera. However, IL-12 microsphere treatment increased vaginal and serum specific IgG antibody (FIG. 4G, H), as well as vaginal specific IgA antibody production (FIG. 4G).

Figure 5:
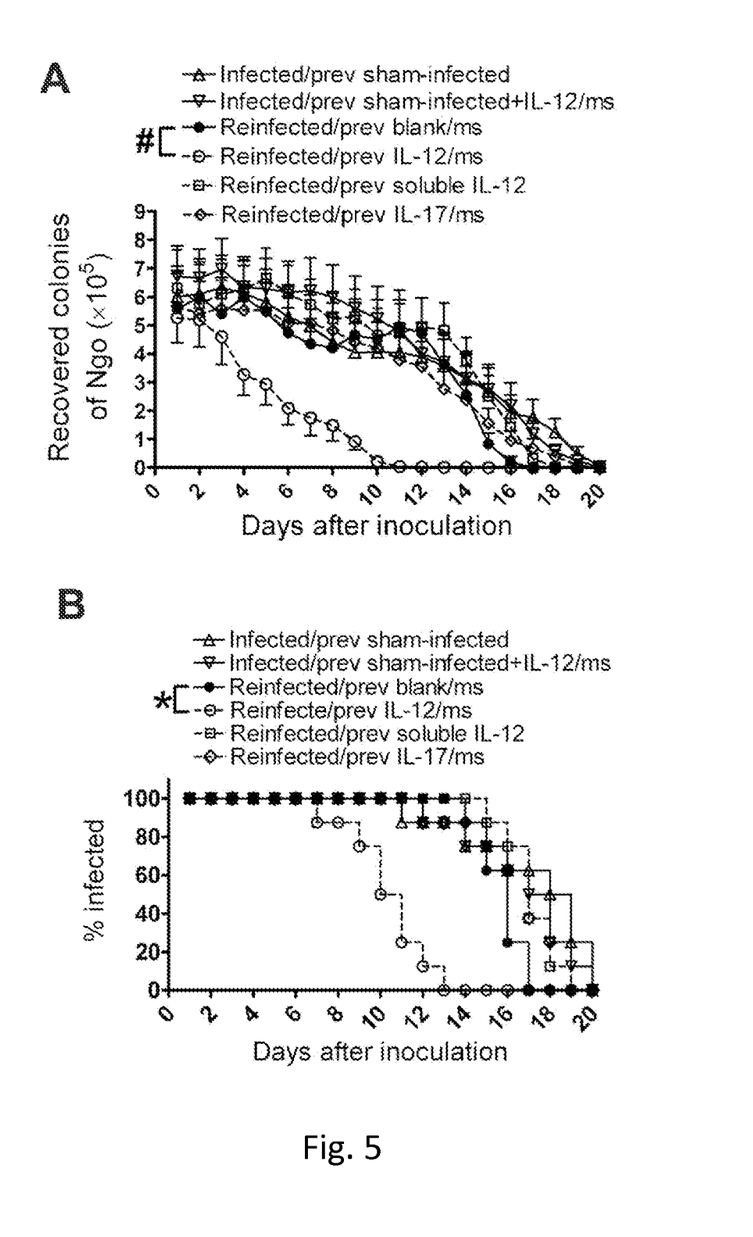

Treatment with IL-12 Microspheres Induces Protective Anamnestic Immunity against Secondary *N. gonorrhoeae* Infection. We further assessed whether IL-12 microsphere treatment resulted in the generation of immune memory and protective immunity against reinfection. Groups of mice infected with *N. gonorrhoeae* were treated with IL-12-loaded or blank microspheres, and after the infection had run its course, the mice were treated with ceftriaxone (300 µg i.p.) on day 15 to ensure complete elimination of the gonococci. An additional group of sham-infected mice treated with IL-12 microspheres was used to evaluate the possible persistent effect of IL-12 in the absence of infection. Five to six weeks later, all mice were inoculated with *N. gonorrhoeae* of the same strain without any further treatment. As observed previously, primary infection of control-treated mice did not protect them against subsequent secondary challenge: the duration and bacterial burden of secondary gonococcal infection in previously blank microsphere-treated mice were the same as for the primary infection of age-matched naïve mice (FIG. 5A, B). In contrast, intravaginal treatment with IL-12-loaded microspheres during primary infection protected the mice against secondary infection: reinfected mice that had been treated with IL-12 microspheres during the primary infection resisted the challenge more effectively than controls (FIG. 5A, B). However, previous IL-12 microsphere treatment of sham-infected mice did not induce protection against subsequent infection (FIG. 5A, B). This result also excluded the possibility that any persisting microspheres still affected the secondary *N. gonorrhoeae* infection.

Flow cytometric and RT-PCR analyses of ILN cells and vaginas taken on day 5 and day 3 of secondary infection, respectively, indicated that the protective effect of previous IL-12 microsphere treatment on secondary gonococcal infection was also associated with significantly enhanced Th1 (IFN-γ) responses (FIG. 5C, D). There was also a robust specific secondary antibody response in IL-12 microsphere-treated mice after they were rechallenged with *N. gonorrhoeae*. Gonococcus-specific IgA and IgG antibodies in vaginal washes and IgG antibodies in sera of reinfected mice previously treated with IL-12 microspheres were significantly higher than those of control groups (FIG. 5E, F).

In contrast to the effects of IL-12 microsphere treatment, treatment with IL-17 microspheres during primary gonococcal infection did not lead to any protective immunity to secondary gonococcal infection, or induce any anamnestic T cell or antibody responses (FIG. 5A-F).

Although the present invention has been described with respect to one or more particular embodiments, it will be understood that other embodiments of the present invention may be made without departing from the spirit and scope of the present invention.

The invention claimed is:

1. A method for treating a genital tract infection in a female subject comprising the steps of:
   a) identifying a subject who is suffering from the infection;
   b) administering to the subject intravaginally, a composition comprising an amount of interleukin-12 (IL-12) incorporated in polymeric microspheres effective to treat the genital tract infection, wherein said composition does not contain a genital tract infection causing microorganism or an antigen therefrom, and wherein administration of the said composition results in treatment of the infection, and wherein the genital tract infection is caused by *N. gonorrhoeae*.

2. The method of claim 1, wherein the amount of IL-12 administered is from 1 µg to 200 µg per dose.

3. The method of claim 2, wherein each dose is administered at intervals of from 1 day to 1 month.

4. The method of claim 1, wherein the subject is not being administered IL-12 by any other administration route.

5. The method of claim 1, further comprising the step of administering an antimicrobial agent to the subject.

6. The method of claim 5, wherein the antimicrobial agent is selected from the group consisting of fluorquinolone, cephalosporin, azithromycin, ceftriaxone, doxycycline, cefixime, and combinations thereof.

7. The method of claim 1, wherein the intravaginal administration of IL-12 does not increase serum IL-12 level to more than 50 picograms/ml.

8. The method of claim 1, wherein the microspheres comprise polylactic acid (PLA).

9. A method for reducing the risk of recurrence of genital tract infections in a female subject comprising the steps of:
   a) identifying a subject who is suffering from the infection;
   b) administering to the subject intravaginally, a composition comprising an amount of interleukin-12 (IL-12) incorporated in polymeric microspheres effective to reduce the recurrence of the infection, wherein said composition does not contain a genital tract infection causing microorganism or an antigen therefrom, and wherein administration of the said composition results in reducing the risk of recurrence of the infection, and wherein the genital tract infection is caused by *N. gonorrhoeae*.

10. The method of claim 9, wherein the amount of IL-12 administered is from 1 µg to 200 µg per dose.

11. The method of claim 10, wherein each dose is administered at intervals of from 1 day to 1 month.

12. The method of claim 9, wherein the microspheres comprise polylactic acid.

13. The method of claim 9, further comprising the step of administering an antimicrobial agent to the subject.

14. The method of claim 13, wherein the antimicrobial agent is selected from the group consisting of fluorquinolone, cephalosporin, azithromycin, ceftriaxone, doxycycline, cefixime, and combinations thereof.

15. A method for treating a genital tract infection in a female subject comprising the steps of:
   a) identifying a subject who is suffering from the infection;
   b) administering to the subject intravaginally, a composition comprising an amount of interleukin-12 (IL-12) incorporated in polymeric microspheres effective to treat the genital tract infection, wherein said composition does not contain any other therapeutic agent, and wherein administration of the said composition results in treatment of the infection, and wherein the genital tract infection is caused by *N. gonorrhoeae*.

16. The method of claim 15, wherein the amount of IL-12 administered is from 1 µg to 200 µg per dose.

17. The method of claim 16, wherein each dose is administered at intervals of from 1 day to 1 month.

18. The method of claim 17, wherein the microspheres comprise polylactic acid.

19. A method for reducing the risk of recurrence of genital tract infections in a female subject comprising the steps of:
   a) identifying a subject who is suffering from the infection;
   b) administering to the subject intravaginally, a composition comprising an amount of interleukin-12 (IL-12) incorporated in polymeric microspheres effective to reduce the recurrence of the infection, wherein said composition does not contain any other therapeutic or prophylactic agent, and wherein administration of the said composition results in reducing the risk of recurrence of the infection, and wherein the genital tract infection is caused by *N. gonorrhoeae*.

20. The method of claim 19, wherein the amount of IL-12 administered is from 1 µg to 200 µg per dose.

21. The method of claim 20, wherein each dose is administered at intervals of from 1 day to 1 month.

22. The method of claim 21, wherein the microspheres comprise polylactic acid.

* * * * *